(12) United States Patent
Hara et al.

(10) Patent No.: US 9,357,774 B2
(45) Date of Patent: Jun. 7, 2016

(54) STERILIZATION METHOD

(75) Inventors: Michikazu Hara, Yokohama (JP);
Takeshi Kadono, Kawasaki (JP);
Takahiro Ishikawa, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 13/390,642

(22) PCT Filed: Aug. 31, 2010

(86) PCT No.: PCT/JP2010/064792
§ 371 (c)(1),
(2), (4) Date: Apr. 3, 2012

(87) PCT Pub. No.: WO2011/025026
PCT Pub. Date: Mar. 3, 2011

(65) Prior Publication Data
US 2012/0190749 A1 Jul. 26, 2012

(30) Foreign Application Priority Data
Aug. 31, 2009 (JP) .................................. 2009-200678

(51) Int. Cl.
*A01N 41/04* (2006.01)
*C02F 1/50* (2006.01)
*A01N 61/00* (2006.01)
*C02F 1/00* (2006.01)

(52) U.S. Cl.
CPC ............... *A01N 41/04* (2013.01); *A01N 61/00* (2013.01); *C02F 1/50* (2013.01); *C02F 1/001* (2013.01)

(58) Field of Classification Search
CPC ........... A01N 41/04; A01N 61/00; C02F 1/50
USPC ........................... 514/577; 210/483; 422/243
See application file for complete search history.

(56) References Cited

U.S. PATENT DOCUMENTS

| 2,086,753 | A  | * | 7/1937  | Urbain et al. .................. 210/668 |
| 5,883,026 | A  |   | 3/1999  | Reader et al. |
| 2003/0092560 | A1 |   | 5/2003  | Von Blucher et al. |
| 2006/0276668 | A1 |   | 12/2006 | Domen et al. |
| 2008/0171648 | A1 |   | 7/2008  | Von Blucher et al. |
| 2008/0227996 | A1 |   | 9/2008  | Hara et al. |
| 2009/0127207 | A1 | * | 5/2009  | Okamoto et al. ............. 210/747 |

FOREIGN PATENT DOCUMENTS

| EP | 1 908 516 A1 | 4/2008 |
| EP | 2 116 510 A1 | 11/2009 |
| EP | 2 159 193 A1 | 3/2010 |
| JP | 4-200634 A | 7/1992 |
| JP | 2001-170482 A | 6/2001 |
| JP | 2003-531800 A | 10/2003 |
| JP | 2005-152560 A | 6/2005 |
| JP | 4041409 B2 | 1/2008 |
| JP | 2009-201634 A | 9/2009 |
| RU | 2 070 438 C1 | 12/1996 |
| RU | 2 343 359 C1 | 1/2009 |
| WO | WO 2005/029508 A1 | 3/2005 |

OTHER PUBLICATIONS

Cornelissen et al., Title: Extensive Sorption of Organic Compounds to black carbon, coal, and Kerogen in sediments and soilds: Mechanisms and consequuences for distribution, bioaccumullation, and bidegradation; Environmental Science and Technology, vol. 39, No. 18, pp. 6881-6895, published on web Aug. 5, 2005).*
ATSDR (Agency for Toxic Substances and Disease Registry), Title: Public health statement on sulfur trioxide and sulfuric acid, published Dec. 1998.*
Servais et al., Titel: Supply of organic matter and bacterial to aquatic ecosystem through waster water effluents, Wat. Res., vol. 33 (16), pp. 3521-3531, 1999.*
Dung et al.; Title: Catalytic Decomposition of Biomass Tars at Low-Temperature, pp. 285-6306, Chapter 11 of Book titled: "Biomass Now—Sustainable Growth and Use", edited by Miodrag Darko Matovic, Published: Apr. 30, 2013. Downloaded from http://cdn.intechopen.com/pdfs-wm/44394.pdf on Nov. 12, 2014.*
Title: How coal is formed? published by Mining services, Inc.; downloaded from http://www.coaleducation.org/q&a/how__coal__formed.htm on Oct. 16, 2015.*
PCT International Preliminary Report on Patentability (PCT/IPEA/409) issued in PCT/JP2010/064792 on Mar. 29, 2012.
PCT/ISA/210—International Search Report dated Dec. 7, 2010 issued in PCT/JP2010/064792.
Benak et al., "Sulfonation of pyropolymeric fibers derived from phenol-formaldehyde resins", Carbon, vol. 40 (2002) pp. 2323-2332.
Supplemental European Search Report issued in European Patent Application No. 10812072.6 on May 16, 2013.
Russian Office Action dated Aug. 6, 2014, issued in corresponding Russian Patent Application No. 2012112394.

* cited by examiner

*Primary Examiner* — Johann R Richter
*Assistant Examiner* — Yanzhi Zhang
(74) *Attorney, Agent, or Firm* — Birch, Stewart, Kolasch & Birch, LLP

(57) ABSTRACT

It is an object of the present invention to provide a novel sterilization method capable of killing not only microorganisms in water, but also microorganisms in a gas. Specifically, the present invention provide a method for sterilizing a gas or liquid, comprising contacting a microorganism in a gas or liquid with a material containing an amorphous carbon having a sulfo group introduced therein.

3 Claims, No Drawings

STERILIZATION METHOD

TECHNICAL FIELD

The present invention relates to a sterilization method for microorganisms such as E. coli, particularly, a sterilization method suitable for drinking water, cleaning water, living space, car interior space, food storage facilities, water utilization facilities, in-room items, and personal belongings. The present invention also relates to a column and a filter used for killing microorganisms. The present invention further relates to a mask preventing inhalation and release of microorganisms.

BACKGROUND ART

For example, as a sterilization method for infectious and pathogenic microorganisms, a heat sterilization method is generally recommended. However, the heating temperature is often limited because in certain cases application of heat treatment is difficult, and also for a fear of heat-induced deterioration in quality, etc. Naturally, the sterilization effect will be limited. Sodium hypochlorite is used in lieu of or in combination with heat sterilization, and also, disinfectant water containing hypochlorous acid is commercially available.

Also, as a conventional example, Patent Literature 1 discloses a sterilization method for microorganisms (E. coli), which is configured in such a way that treatment is conducted so that the heating temperature is at 60° C. or below in the presence of allyl isothiocyanate. Patent literature 2 discloses a sterilization method for microorganisms in water utilization facilities, which is configured in such a way that silver ions and copper ions, silver ions and residual chlorine, copper ions and residual chlorine, or silver ions, copper ions, and residual chlorine are allowed to coexist.

CITATION LIST

Patent Literature

Patent Literature 1: Japanese Patent Laid-Open No. 11-322521
Patent Literature 2: Japanese Patent Laid-Open No. 2007-268402

SUMMARY OF INVENTION

Technical Problem

An object of the present invention is to provide a novel sterilization method capable of killing not only particularly microorganisms in water, but also microorganisms in a gas as well, compared to the sterilization method disclosed in each of the aforementioned Patent Literatures.

Solution to Problem

The present inventors have earnestly studied to achieve the aforementioned object. As a result, they have found that a material containing an amorphous carbon having a sulfo group introduced therein, which is employed for a solid acid catalyst, a proton conducting membrane of a fuel cell, and the like, exhibits a strong sterilization effect against microorganisms in a gas or liquid.

Although a liquid acid is well known to exhibit a sterilization effect on microorganisms, unlike a liquid acid, a solid acid is considered to have less frequent contact with microorganisms due to its lack of fluidity. Accordingly, at the time of filing of the present application, a solid acid was assumed not to have a sterilization effect as is exhibited by a liquid acid. Thus, the fact that a material containing an amorphous carbon having a sulfo group introduced therein exhibits a strong sterilization effect was entirely unpredictable to those skilled in the art.

The present inventors have also found that a material containing an amorphous carbon having a sulfo group introduced therein not only simply kills microorganisms, but also has an action of hydrolyzing the components of microorganisms.

The present invention was completed based on the foregoing findings.

That is, the present invention provides the following [1] to [9].

[1] A method for sterilizing a gas or liquid, comprising contacting a microorganism in a gas or liquid with a material containing an amorphous carbon having a sulfo group introduced therein.

[2] The method for sterilizing a gas or liquid according to [1], wherein the gas or liquid is passed through a column filled with the material containing an amorphous carbon having a sulfo group introduced therein.

[3] The method for sterilizing a gas or liquid according to [1], wherein the gas or liquid is passed through a filter supporting the material containing an amorphous carbon having a sulfo group introduced therein.

[4] The method for sterilizing a gas or liquid according to [1], wherein the material containing an amorphous carbon having a sulfo group introduced therein is obtained by condensation and sulfonation of an incompletely carbonized organic compound through heat treatment with sulfur trioxide or a sulfonating agent containing sulfur trioxide.

[5] The method for sterilizing a gas or liquid according to [1], wherein the material containing an amorphous carbon having a sulfo group introduced therein is obtained by condensation and sulfonatation of at least one selected from the group of polycyclic aromatic hydrocarbons having condensed 2 or more and 7 or less aromatic rings through heat treatment in a concentrated or fuming sulfuric acid.

[6] The method for sterilizing a gas or liquid according to [1], wherein the material containing an amorphous carbon having a sulfo group introduced therein is obtained by introducing a sulfo group in an organic compound through heat treatment in a concentrated or fuming sulfuric acid, and the material has the following properties; (1) chemical shifts of a condensed 6-membered aromatic carbon ring and a condensed 6-membered aromatic carbon ring having a sulfo group bound thereto are detected in a $^{13}C$ nuclear magnetic resonance spectrum, (2) at least a diffraction peak of a carbon (002) plane whose half-value width ($2\theta$) is 5 to 30° in powder X-ray diffraction is detected, and (3) it exhibits proton conductivity.

[7] A column for sterilization, wherein the column is filled with a material containing an amorphous carbon having a sulfo group introduced therein.

[8] A filter for sterilization, wherein the filter supports a material containing an amorphous carbon having a sulfo group introduced therein.

[9] A mask comprising an air-permeable member, wherein the air permeable member supports a material containing an amorphous carbon having a sulfo group introduced therein.

Advantageous Effects of Invention

The sterilization method of the present invention can exert a high sterilization effect without requiring electric power or heat energy. Therefore, it is useful as a sterilization method in the area where there is a shortage of electric power supply and the like, and it is also advantageous in that it imposes a low environmental load.

DESCRIPTION OF EMBODIMENTS

Hereinbelow, the present invention will be described in detail.

The method for sterilizing a gas or liquid of the present invention comprises contacting a microorganism in a gas or liquid with a material containing an amorphous carbon having a sulfo group introduced therein.

This material containing an amorphous carbon having a sulfo group introduced therein exhibits properties such as showing strong acidity, not causing elution of acid even when it is put into a polar solvent (such as water, alcohol, aldehyde, carboxylic acid, and ketone), thereby not affecting the quality of water unlike chemical sterilization, and not causing elution in a gas such as air either.

The material containing an amorphous carbon having a sulfo group introduced therein which can be used herein includes the following carbonaceous solid acids A to C.

The carbonaceous solid acid A is a solid acid obtained by condensation and sulfonation of an incompletely carbonized organic compound through heat treatment with sulfur trioxide or a sulfonating agent containing sulfur trioxide. An application pertaining to this carbonaceous solid acid A has been previously filed in Japan (Japanese Patent Application No. 2009-134096).

Here, the organic compound may be waste wood or sawdust; however, at least one polycyclic aromatic hydrocarbon selected from benzene, anthracene, perylene, coronene, and sulfo compounds thereof is preferably used. Further, heavy fuel oil, pitch, tar, asphalt, and the like containing aromatic hydrocarbons can also be used. The aforementioned organic compounds may be used alone, or a mixture of plural kinds of two or more kinds of the above organic compounds may also be used. The incompletely (not perfectly) carbonized organic compound refers to an amorphous carbon composed of polycyclic aromatic hydrocarbon consisting of 10 to 20 aromatic 6-membered rings, and one example is an amorphous carbon in which 10 to 20 benzene rings are aligned. The incompletely carbonized organic compound is obtained by, for example, heating an organic compound at 200 to 600° C., preferably at 300 to 500° C. for 0.5 to 20 hours, preferably for 1 to 10 hours. There are many carbon-hydrogen bonds still left in an organic compound obtained as above, and when it is subjected to sulfonation, a sulfo group is bound to this carbon-hydrogen bonding site. Therefore, an incompletely carbonized organic compound is used so as to obtain a solid acid with a higher density of sulfo groups. In light of the above, the incompletely carbonized organic compound desirably contains many carbon-hydrogen bonds, in other words, desirably contains a large amount of hydrogen. The amount of hydrogen in the incompletely carbonized organic compound is preferably 0.3 to 1.5, more preferably 0.5 to 1.1 in terms of the element ratio of hydrogen to carbon (H/C, an atomic ratio).

The chemical formula of sulfur trioxide is $SO_3$, which is also referred to as anhydrous sulfuric acid. When contacting sulfur trioxide with an incompletely carbonized organic compound, it is important to carry out this process under a stream of an inert gas such as nitrogen and argon, or under a stream of dry air for the production of a solid acid with a high density of sulfo groups.

One example of the sulfonating agent containing sulfur trioxide can be a fuming sulfuric acid.

The carbonaceous solid acid B is a solid acid obtained by condensation and sulfonation of at least one selected from the group of polycyclic aromatic hydrocarbons having condensed 2 or more and 7 or less aromatic rings through heat treatment in a concentrated or fuming sulfuric acid. An application pertaining to this carbonaceous solid acid B has previously been filed and a patent has been granted in Japan (Japanese Patent No. 40414909). The properties, production methods, and the like of this carbonaceous solid acid B are described in this Japanese Patent Publication No. 40414909.

Here, examples of the polycyclic aromatic hydrocarbon include naphthalene, anthracene, perylene, and coronene, and as long as two or more aromatic rings are condensed, any of such polycyclic aromatic hydrocarbons can be used as a synthetic raw material of the carbonaceous solid acid B. It is known that aromatic hydrocarbons undergo polycondensation in a concentrated or fuming sulfuric acid to form an amorphous material of highly-condensed, complex polycyclic aromatic hydrocarbon, and that the property of the resulting amorphous material becomes closer to that of graphite with an increase in the number of the aromatic ring, and the like. Also, the carbonaceous solid acid of the present invention has a stable chemical structure, which is obtained by condensation and sulfonation of a polycyclic aromatic hydrocarbon through heat treatment of a polycyclic aromatic hydrocarbon, particularly at least one selected from the group of polycyclic aromatic hydrocarbons having condensed 2 or more and 7 or less aromatic rings, in a concentrated or fuming sulfuric acid.

A sulfonated polycyclic aromatic hydrocarbon having many polycondensed aromatic rings is obtained by sulfonation and polycondensation of a polycyclic aromatic hydrocarbon through heat treatment in a concentrated or fuming sulfuric acid. However, when the temperature of the treatment in a concentrated or fuming sulfuric acid is lower than 100° C., polycondensation of polycyclic aromatic hydrocarbon does not sufficiently proceed, failing to form a polycyclic aromatic hydrocarbon composed of many aromatic rings, and thereby failing to produce a solid acid that is insoluble in a polar solvent. Meanwhile, when the treatment temperature exceeds 450° C., thermal decomposition of a sulfo group takes place, failing to produce an insoluble amorphous hydrocarbon containing sufficient sulfo groups. A more preferred treatment temperature is 200° C. to 350° C. The solid acid catalyst of the present invention can be synthesized by using not only a single polycyclic aromatic hydrocarbon as the raw material, but also plural polycyclic aromatic hydrocarbons as the raw material. Further, it can also be synthesized by using pitch, tar, and the like containing various kinds of polycyclic aromatic hydrocarbons as well as saturated hydrocarbon and unsaturated hydrocarbon as the raw material.

The carbonaceous solid acid C is a solid acid obtained by introducing a sulfo group by subjecting an organic compound to heat treatment in a concentrated or fuming sulfuric acid. An international application pertaining to this carbonaceous solid acid C has been previously filed (WO 2005/029508). The properties, production methods, and the like of this carbonaceous solid acid C are described in International Publication No. WO 2005/029508.

Here, as the organic compound, aromatic hydrocarbons can be used; however, other organic compounds, for example, saccharides such as glucose, sugar (sucrose), and cellulose, and synthetic polymer compounds such as polyethylene and polyacrylamide may also be used. The aromatic hydrocarbons are either polycyclic aromatic hydrocarbons or monocyclic aromatic hydrocarbons, and for example, benzene, naphthalene, anthracene, perylene, and coronene can be used, of which naphthalene and the like can preferably be used. Although the organic compound may be used singly, a combination of two or more kinds thereof may also be used. Also, a purified organic compound need not necessarily be used, and for example, heavy fuel oil, pitch, tar, and asphalt containing aromatic hydrocarbons may also be used.

When saccharides such as glucose and cellulose and synthetic polymer compounds are used as the raw material, it is preferable to heat these raw materials in a stream of an inert gas to partially carbonate them in advance before heat treatment in a concentrated or fuming sulfuric acid. The heating temperature in this heat treatment is normally 200 to 600° C. and the treatment time is normally 0.5 to 20 hours. A condition of Partial carbonation is preferably such that a diffraction peak of a (002) plane whose half-value width (2θ) is 30 is detected in a powder X-ray diffraction pattern of the heat treated product.

When aromatic hydrocarbons or heavy fuel oil, pitch, tar, asphalt, and the like containing aromatic hydrocarbons are used as the raw material, it is preferable to subject a product resulting from heat treatment in a concentrated or fuming sulfuric acid to vacuum heating. This process removes excess sulfuric acid, while promoting carbonization and solidification of the product, whereby increasing the yield of the product. For evacuation, an exhauster with an exhausting speed of 10 L/min or more and an ultimate pressure of 100 torr or less is preferably used. A preferred heating temperature is 140 to 300° C., and a more preferred temperature is 200 to 280° C. The time of evacuation at this temperature is normally 2 to 20 hours.

This carbonaceous solid acid C has the following characteristics (1) to (3).
(1) Chemical shifts of a condensed 6-membered aromatic carbon ring and a condensed 6-membered aromatic carbon ring having a sulfo group bound thereto are detected in a $^{13}C$ nuclear magnetic resonance spectrum.
(2) At least a diffraction peak of a carbon (002) plane whose half-value width (2θ) is 5 to 30° in powder X-ray diffraction is detected. Also, the detected diffraction peaks may include a peak corresponding to other than a (002) plane; however, preferably, only a diffraction peak of a (002) plane is detected.
(3) It exhibits proton conductivity. In this case, although no particular limitation is imposed on the proton conductivity, it is preferably 0.01 to 0.2 $Scm^{-1}$, more preferably 0.08 to 0.11 $Scm^{-1}$ (the aforementioned proton conductivity is a value as measured by an alternating current impedance method under conditions of a temperature of 80° C. and a humidity of 100%).

No particular limitation is imposed on a method for contacting a microorganism in a gas or liquid with a material containing an amorphous carbon having a sulfo group introduced therein. Examples thereof include a method of passing a gas or liquid to be sterilized through a column filled with a material containing an amorphous carbon having a sulfo group introduced therein, a method of passing a gas or liquid to be sterilized through a filter supporting a material containing an amorphous carbon having a sulfo group introduced therein, and a method of mixing a gas or liquid to be sterilized with a material containing an amorphous carbon having a sulfo group introduced therein, followed by stirring.

The column which can be used herein includes a column having an inflow port through which a gas or liquid to be sterilized is infused, an outflow port through which a sterilized gas or liquid is discharged, and a part to be filled with a material containing an amorphous carbon having a sulfo group introduced therein. For the column for sterilization, a column employed for chromatography and the like may also be used.

The filter which can be used herein includes a filter which has fine holes or openings so that a gas or liquid can pass through the filter, and which can support a material containing an amorphous carbon having a sulfo group introduced therein. Specifically, a woven or non-woven fabric and the like which supports a material containing an amorphous carbon having a sulfo group introduced therein can be used. Any woven or non-woven fabric may be used as long as it is resistant against acid.

Examples of the utility of the sterilization method of the present invention include the following. Unsterilized water is passed through the aforementioned column for sterilization so that it is provided as drinking water or cleaning. The aforementioned filter is installed at a ventilation fan or at a ventilating opening in the living space, car interior space, food storage facilities, and the like to prevent microorganisms from invading the room. An air cleaner having the aforementioned filter is installed in the living space, car interior space, food storage facilities, and the like to eliminate microorganisms in the room. Also, the aforementioned filter or column is installed at a water circulation part in water utilization facilities such as a pool to sterilize water.

The sterilization method of the present invention can also be utilized for a mask. That is, if a breathable member (for example, a woven or non-woven fabric) that is resistant to acid is supported with a material containing an amorphous carbon having a sulfo group introduced therein and a mask is producing using the resulting member, then it will be provided as a mask capable of preventing inhalation and release of microorganisms.

In the present invention, the microorganism refers to an organism generally called a microorganism, for example, bacteria, archaea, protozoa, and fungi, and further, it also includes unicellular eukaryotic algae having flagella such as Euglena, and moreover, viruses.

The mechanism of action of the sterilization effect of the material containing an amorphous carbon having a sulfo group introduced therein has not been elucidated in detail yet; however, given that this material has a sulfo group, which is converted to a strong acid site that is comparable to sulfuric acid, the sterilization effect is assumed to be exerted through contact of the microorganisms to this sulfo group. Because this material is carbonaceous, it is adsorptive to microorganisms, and it is considered that the microorganisms in a gas or liquid are attracted toward this adsorptivity, whereby the microorganisms are efficiently brought into contact with a sulfo group. As described above, a solid acid has been considered to be devoid of a sterilization effect because, unlike a liquid acid, it lacks fluidity; however, this material containing an amorphous carbon having a sulfo group introduced therein is considered to have solved the problem of fluidity owing to its adsorptivity to microorganisms.

Also, in the Examples to be described later, only the sterilization effect on the microorganisms in a liquid is demonstrated. However, if the mechanism of action of the sterilization effect of the material containing an amorphous carbon having a sulfo group introduced therein is supposed to be as described above, then it is assumed to exert a similar sterilization effect also on the microorganisms in a gas as it does on the microorganisms in a liquid.

EXAMPLES

Next, the sterilization effect of the present invention will be elucidated with reference to Examples.

Example 1

In this Example, the sterilization effect of the carbonaceous solid acids A to C produced by the following methods on *E. coli* was examined.

(1) Production of the Carbonaceous Solid Acid A

As the organic compound, commercially available microcrystalline cellulose was used. Into a three neck flask, 20 g of this cellulose was placed, followed by heating at 450° C. for five hours under a stream of nitrogen gas, whereby 9 g of an incompletely carbonized product was obtained (hereinbelow, this product is referred to as an "incomplete carbide"). This operation was repeated to secure a certain weight of incomplete carbide. Into a 1 L recovery flask, 20.2 g of the incomplete carbide obtained as above was placed, and the flask was then mounted on the rotary evaporator ROTAVAPOR RE120 (manufactured by BUCHI Labortechnik AG (Switzerland)). The recovery flask was rotated while heating to 60° C., and at the same time, the inside of the evaporator was deaerated by a vacuum pump (0.5 kPa), and the flask was hermetically sealed. Meanwhile, 6.1 g of sulfur trioxide (trade name "Nisso Sulfan" supplied by NISSO METALLOCHEMICAL CO., LTD.) was weighed out and placed in a three neck flask for gasification. This sulfur trioxide was gradually introduced into the evaporator from an injection cock in the upper part of the condenser of the rotary evaporator. After introduction of sulfur trioxide, reactions were allowed to proceed while rotating the recovery flask at 60° C. for two hours. Upon completion of the reaction, a sulfur trioxide gas-introduction line was disconnected and the sulfur trioxide gas in the evaporator was replaced by nitrogen gas. The recovery flask was disconnected from the evaporator and approximately 500 mL of distilled water was added into the recovery flask, followed by stirring for 10 minutes. The temperature was maintained at 30° C. or below. Subsequently, the solid content was filtered by suction filtration using a hydrophilic PTFE filter (manufactured by Millipore Corporation, omnipore, pore size of 10 µm). As aqueous washing, the solid content was resuspended in an approximately 500 mL of distilled water, followed by stirring for 10 minutes, and the solid was filtered again. This operation was repeated until the pH of the filtrate was almost constant, and then the solid content was dried at 80° C. for a day. Further, as hot water washing, the solid content was washed with 500 mL of distilled water of approximately 100° C. This operation was repeated until the pH of the filtrate was almost constant. After hot water washing, the solid content was dried at 80° C. for a day to give 20.9 g of a solid acid. The sulfur content in the carbonaceous solid acid A obtained as above was 0.94 wt. %.

(2) Production of the Carbonaceous Solid Acid B

The carbonaceous solid acid B was produced in accordance with the description of Example 1 of Japanese Patent No. 4041409. Specifically, the production was as follow. As a polycyclic aromatic hydrocarbon, commercially available coronene ($C_{24}H_{12}$) was used. Into 100 mL of concentrated sulfuric acid (96%), 1 g of coronene was added, followed by heating at 200° C. for eight hours. Then, excess concentrated sulfuric acid was removed by distillation under reduced pressure at 250° C. to give black solid powder. The solid powder thus obtained was washed with 300 mL of ethyl alcohol, and this operation was repeated until sulfuric acid in ethyl alcohol after washing was equal to or below the detection limit of the elementary analysis. The carbonaceous solid acid B was obtained as black powder and no structure was confirmed by an X-ray diffraction pattern, revealing that it was amorphous. Also, the sulfur content in the carbonaceous solid acid B obtained as above was 4 wt. %.

(3) Production of the Carbonaceous Solid Acid C

The carbonaceous solid acid C was produced in accordance with the description of Example 4 in the specification of WO 2005/029508. Specifically, the production was as follows. As the organic compound, commercially available naphthalene was used. Into 300 mL of 96% concentrated sulfuric acid, 20 g of naphthalene was added, and while infusing nitrogen gas into the resulting mixture at 30 ml/min, the mixture was heated at 250° C. for 15 hours to give a black liquid. The liquid thus obtained was heated at 250° C. for five hours while evacuating using a high vacuum rotary pump with an exhausting speed of 50 L/min and an ultimate pressure of $1\times10^{-2}$ torr or less to remove excess concentrated sulfuric acid and promote carbonization, whereby black powder was obtained. The black powder thus obtained was heated at 180° C. for 12 hours under a stream of an inert gas, and then washed with 300 mL of distilled water. This operation was repeated until sulfuric acid in distilled water after washing was equal to or under the detection limit of the aforementioned elementary analysis by an elementary analyzer using flash combustion, whereby an amorphous carbon having a sulfo group introduced therein, namely a carbonaceous solid acid was obtained. As a result of measurement of the resulting carbonaceous solid acid by the $^{13}$CMAS nuclear magnetic resonance spectrometry, a chemical shift due to a condensed 6-membered aromatic carbon ring appeared near 130 ppm and a chemical shift due to a sulfo group-bound condensed 6-membered aromatic carbon ring appeared near 140 ppm in a $^{13}$C nuclear magnetic resonance spectrum. These shifts are spinning sidebands that are characteristically observed in the $^{13}$C MAS nuclear magnetic resonance spectrometry, and are not originated from carbon species. Also, as a powder X-ray diffraction pattern, diffraction peaks of the carbon (002) and (004) planes were confirmed by measurement with an X-ray analyzing device. The half-value width (2θ) of diffraction peaks of the (002) plane was 11°. Also, the sulfur content in the carbonaceous solid acid C obtained as above was 9 wt. %.

(4) Sterilization Effect of the Carbonaceous Solid Acids A to C on *E. coli*

(i) As *E. coli*, *Escherichia coli* NBRC3972 obtained from National Institute of Technology and Evaluation was used. A test bacterial liquid was obtained by suspending bacterial bodies obtained by culturing the aforementioned *E. coli* in a normal agar plate medium (manufactured by NISSUI PHARMACEUTICAL CO., LTD.) at 30° C. for one day in sterilized water, and then adjusting the bacterial count to approximately $2\times10^7$ cfu/ml (cfu stands for colony forming unit).

(ii) As the medium for bacterial count measurement, a large number of agar plate media were produced by adding 1.5% agar to the SCDLP medium "Daigo" (manufactured by NIHON PHARMACEUTICAL CO., LTD) and used.

(iii) The measurement operation is as follows: 0.1 g of the powdery carbonaceous solid acid A was weighed out and placed in a vial with a SILICOSEN, followed by steam sterilization at 121° C. for 15 minutes. After this sterilization treatment, 2 ml of the aforementioned test bacterial liquid was added into the vial, followed by rotary shaking at 30° C. (140 rpm). After 10 minutes, 200 µl of the liquid thus treated in the vial (the carbonaceous solid acid A+the test bacterial liquid) was sampled, which was then immediately serially diluted (10 to $10^4$-fold dilution) with sterilized water. Subsequently, 50 µl of each dilution of the bacterial liquid was smeared separately onto the aforementioned SCDLP agar plate medium. After smearing, the bacteria were statically cultured at 30° C. for one to two days and then live bacteria were counted by a colony count method. Similar measurements were also made for the carbonaceous solid acids B and C.

(iv) Also, as a control experiment, the following experiment was also carried out. Into a steam-sterilized vial with a SILICOSEN, 2 ml of the aforementioned test bacterial liquid was placed, followed by rotary shaking at 30° C. (140 rpm). After 10 minutes, 200 μl of the test bacterial liquid in the vial was sampled, which was then immediately serially diluted (10 to $10^4$-fold dilution) with sterilized water. Subsequently, 50 μl of each dilution of the bacterial liquid was smeared separately onto the aforementioned SCDLP agar plate medium. Subsequently, after one to two days of static culture at 30° C., live bacteria were counted by a colony count method.

Table 1 shows the results thus obtained. Also, the number of live bacteria in a test bacterial liquid without performing 10-minute rotary shaking treatment was counted by a colony count method, and the resulting bacterial count was shown in Table 1 as the live bacterial count at the initiation of the treatment. The live bacterial count in Table 1 represents the value per ml of the treatment liquid, and indicates an average value of the live bacterial count obtained after performing each treatment experiment twice.

TABLE 1

| Solid acid | Live bacterial count (cfu/ml) | |
| --- | --- | --- |
|  | At initiation of treatment | After 10-minute treatment |
| No carbonaceous solid acid | $2.2 \times 10^7$ | $1.9 \times 10^7$ |
| Carbonaceous solid acid A | $2.2 \times 10^7$ | 0 |
| Carbonaceous solid acid B | $2.2 \times 10^7$ | 0 |
| Carbonaceous solid acid C | $2.2 \times 10^7$ | 0 |

Example 2

In this Example, using Euglena belonging to the genus Euglena from among those of the phylum Euglenozoa and the phylum Protozoa, the sterilization effect (cell membrane disrupting effect) of each of the carbonaceous solid acids A to C was examined under the following conditions.

(1) Production of the Carbonaceous Solid Acids A to C

The carbonaceous solid acids A to C were produced in a similar manner to Example 1.

(2) Cell Membrane Disrupting Effect of the Carbonaceous Solid Acids A to C on Euglena (i) As the test bacteria, Euglena (powder) obtained from EUGLENA CO., LTD. was used. The above cell membrane disrupting effect was confirmed by a phenomenon of detecting intracellular glucose in the Euglena cell along with the disruption of Euglena.

(ii) The test method is as follows: 3 g of the carbon solid acid A, 1.5 g of the aforementioned Euglena, and 2.5 ml of water were weighed out and placed in a beaker, followed by stirring at 30° C. for one hour (400 rpm). Then, the sterilization effect was judged by measuring glucose in the resulting aqueous solution. As a Comparative Example, a similar test was performed by replacing the carbonaceous solid acid with strongly acidic ion exchange resin (manufactured by Aldrich, Amberlyst-15). The carbonaceous solid acids B and C were also similarly tested.

From the above tests, it was found that when the carbonaceous solid acid A was used, 53 mg of glucose was detected, and when the carbonaceous solid acid B was used, 20 mg of glucose was detected, and when the carbonaceous solid acid C was used, 25 mg of glucose was detected. In contrast, when the strongly acidic ion exchange resin was used, no glucose was deleted.

Example 3

In this Example, the sterilization effect of the carbonaceous solid acid D produced by the following method on various microorganisms was examined.

(1) Production of the Carbonaceous Solid Acid D

Into a 500 mL three neck flask, 4 g of the aforementioned incomplete carbide, 100 mL of 96% concentrated sulfuric acid, and 100 mL of 30% fuming sulfuric acid were placed, followed by heating at 80° C. for 10 hours under a stream of nitrogen. After 10 hours, the resulting mixture was returned to room temperature, to which 200 mL of distilled water was added, and the solid content was filtered by suction filtration using a glass fiber filter. The solid content was collected and resuspended in 400 mL of distilled water of approximately 100° C. After heating and stirring for 30 minutes, the solid content was filtered by suction filtration. This operation was repeated until the pH of the filtrate was almost constant, and then the solid content was dried at 80° C. for a day. After drying, similarly to the above, the solid content was subjected to hot water washing with 400 mL of distilled water of approximately 100° C., and this operation was repeated until the pH of the filtrate was almost constant. After hot water washing, the solid content was dried at 80° C. for a day to give a solid acid. The sulfur content in the carbonaceous solid acid D obtained as above was 5.1 wt. %.

(2) The Sterilization Effect of the Carbonaceous Solid Acid D on Various Microorganisms (i) As the test bacteria, *Pseudomonas putida* NBRC14164, *Staphylococcus aureus* subsp. *aureus* NBRC12732, and *Bacillus atrophaeus* NBRC13721 obtained from National Institute of Technology and Evaluation were used. Test bacterial liquids were obtained by suspending bacterial bodies obtained by culturing each of the microorganisms in an agar plate medium, which was prepared by adding 1.5% agar to the SCDLP medium "Daigo" (manufactured by NIHON PHARMACEUTICAL CO., LTD), at 30° C. (37° C. for the microorganisms belonging to the genus *Staphylococcus*) for one day in sterilized water, and adjusting the bacterial count to approximately $10^5$ to $10^7$ cfu/ml (cfu stands for colony forming unit).

(ii) As the medium for bacterial count measurement, similarly, a large number of SCDLP agar plate media were prepared and used.

(iii) The measurement operation is as follows: 0.1 g of the powdery carbonaceous solid acid A was weighed out and placed in a vial with a SILICOSEN, followed by steam sterilization at 121° C. for 15 minutes. After this sterilization treatment, 2 ml of each of the aforementioned test bacterial liquids was added into the vial, followed by rotary shaking at 30° C. (140 rpm). After 10 minutes, 100 μl of the liquid thus treated in the vial was sampled, which was then immediately serially diluted (10 to $10^4$-fold dilution) with sterilized water. Subsequently, 50 μl of each dilution of the bacterial liquid was smeared separately onto the aforementioned SCDLP agar plate medium. After smearing, the bacteria were statically cultured at 30° C. (37° C. for the microorganisms belonging to the genus *Staphylococcus*) for one to two days and then live bacteria were counted by a colony count method.

(iv) Also, as a control experiment, 2 ml of each of the aforementioned test bacterial liquids was placed in a steam-sterilized vial with a SILICOSEN, followed by rotary shaking at 30° C. (140 rpm). After 10 minutes, 100 μl of the test bacterial liquid in the vial was sampled, and live bacteria were counted by a colony count method in a similar manner to the above.

Table 2 shows the results thus obtained. Also, the number of live bacteria in each of the test bacterial liquids without performing 10-minute rotary shaking treatment was counted by a colony count method, and the resulting bacterial count was shown in Table 2 as the live bacterial count at the initiation of the treatment. The live bacterial count in Table 2 represents the value per ml of the treatment liquid, and indicates an average value of the live bacterial count obtained after performing each treatment experiment twice.

TABLE 2

| Test bacteria | Solid acid | Live bacterial count (cfu/ml) | |
|---|---|---|---|
| | | At initiation of treatment | After 10-minute treatment |
| Pseudomonas putida NBRC14164 | Absent | $1.1 \times 10^7$ | $4.4 \times 10^6$ |
| | Present | $1.1 \times 10^7$ | 0 |
| Staphylococcus aureus NBRC12732 | Absent | $7.3 \times 10^6$ | $7.5 \times 10^6$ |
| | Present | $7.3 \times 10^6$ | 0 |
| Bacillus atrophaeus NBRC13721 | Absent | $3.8 \times 10^5$ | $2.4 \times 10^4$ |
| | Present | $3.8 \times 10^5$ | 0 |

Example 4

In this Example, using $E.$ $coli$, the sterilization effect of the carbonaceous solid acid D was examined under the following conditions.

(1) Preparation of the Carbonaceous Solid Acid D

The carbonaceous solid acid D was prepared in a similar manner to Example 3.

(2) The Sterilization Effect of the Carbonaceous Solid Acid D on $E.$ $coli$ (i) The same $E.$ $coli$ as those used in Example 1 were used.

(ii) As the medium for bacterial count measurement, a tryptosoya agar medium (manufactured by NISSUI PHARMACEUTICAL CO., LTD.) was used.

(iii) The measurement operation is as follows: 0.5 g of the powdery carbonaceous solid acid D was weighed out and placed in a steam-sterilized vial with a SILICOSEN. Then, 10 ml of the aforementioned $E.$ $coli$ liquid was added into the vial, followed by rotary shaking at 25° C. (140 rpm). After three hours, 100 μl of the liquid thus treated in the vial was sampled, which was then immediately serially diluted (10 to $10^3$-fold dilution) with sterilized water. Subsequently, 50 μl of each dilution of the bacterial liquid was smeared separately onto the aforementioned tryptosoya agar plate medium. After smearing, the bacteria were statically cultured at 30° C. for one day and then live bacteria were counted by a colony count method.

(iv) Also, as a control experiment, 10 ml of the aforementioned $E.$ $coli$ liquid was placed in a steam-sterilized vial with a SILICOSEN, followed by rotary shaking at 25° C. (140 rpm). After three hours, 100 μl of the $E.$ $coli$ liquid in the vial was sampled, and live bacteria were counted by a colony count method in a similar manner to the above.

Table 3 shows the results thus obtained. Also, the number of live bacteria in the test bacterial liquid without performing 3-hour rotary shaking treatment was counted by a colony count method, and the resulting bacterial count was shown in Table 3 as the live bacterial count at the initiation of the treatment. The live bacterial count in Table 3 represents the value per ml of the treatment liquid, and indicates an average value of the live bacterial count obtained after performing each treatment experiment twice. Also, pH of each liquid is shown in parentheses.

TABLE 3

| | Live bacterial count (cfu/ml) | |
|---|---|---|
| Solid acid | At initiation of treatment | After 3-hour treatment |
| Absent | $1.6 \times 10^5$ (pH 5.7) | $1.6 \times 10^5$ (pH 8.7) |
| Present | $1.6 \times 10^5$ (pH 5.7) | 0 (pH 8.2) |

INDUSTRIAL APPLICABILITY

The sterilization method of the present invention does not require electric power, heat energy, or the like. Therefore, it is useful for preparation of drinking water or cleaning water in the area where there is a shortage in the electric power and fossil fuel supply.

The invention claimed is:

1. A method for sterilizing a gas or liquid, comprising:
   contacting a microorganism in the gas or liquid with a material containing an amorphous carbon, wherein the amorphous carbon is sulfonated,
   wherein the material containing the amorphous carbon is obtained by condensation and sulfonation of a saccharide through heat treatment with sulfur trioxide or a sulfonating agent containing sulfur trioxide, wherein the element ratio of hydrogen to carbon of the saccharide is 0.3 to 1.5,
   wherein the material containing the amorphous carbon is obtained by condensation and sulfonation of at least one polycyclic aromatic hydrocarbon having 2 to 7 aromatic rings condensed through heat treatment in a concentrated or fuming sulfuric acid, or
   wherein the material containing the amorphous carbon is obtained by introducing a sulfo group into aromatic hydrocarbons or partially carbonized saccharides through heat treatment in a concentrated or fuming sulfuric acid, and the material containing the amorphous carbon has the following properties; (1) chemical shifts of a condensed 6-membered aromatic carbon ring and a condensed 6-membered aromatic carbon ring having a sulfo group bound thereto are detected in a $^{13}C$ nuclear magnetic resonance spectrum, (2) at least a diffraction peak of a carbon (002) plane whose half-value width (2θ) is 5 to 30° in powder X-ray diffraction is detected, and (3) it exhibits proton conductivity;
   wherein sulfuric acid is not eluted into the gas or liquid.

2. The method for sterilizing a gas or liquid according to claim 1, wherein the gas or liquid is contacted with the material containing an amorphous carbon by passing the gas or liquid through a column filled with the material containing an amorphous carbon.

3. The method for sterilizing a gas or liquid according to claim 1, wherein the gas or liquid is contacted with the material containing an amorphous carbon by passing the gas or liquid through a filter supporting the material containing an amorphous carbon.

* * * * *